(12) United States Patent
Spitaleri

(10) Patent No.: US 8,277,419 B1
(45) Date of Patent: Oct. 2, 2012

(54) CATHETER SECUREMENT ASSEMBLY

(76) Inventor: Anthony Spitaleri, LaCrosse, FL (US)

( * ) Notice: Subject to any disclaimer, the term of this patent is extended or adjusted under 35 U.S.C. 154(b) by 1709 days.

(21) Appl. No.: 10/160,555

(22) Filed: May 31, 2002

(51) Int. Cl.
*A61M 5/32* (2006.01)

(52) U.S. Cl. ........................... 604/174; 604/179

(58) Field of Classification Search .......... 604/174, 604/179; 128/DIG. 6, DIG. 26
See application file for complete search history.

(56) References Cited

U.S. PATENT DOCUMENTS

| | | | |
|---|---|---|---|
| 3,161,199 A | 12/1964 | Shaw | |
| 3,648,703 A | 3/1972 | Manker | |
| 4,190,054 A | 2/1980 | Brennan | |
| 4,282,871 A | 8/1981 | Chodorow et al. | |
| 4,316,461 A * | 2/1982 | Marais et al. | 604/179 |
| 4,324,237 A * | 4/1982 | Buttaravoli | 602/54 |
| 4,416,664 A * | 11/1983 | Womack | 604/174 |
| 4,449,975 A * | 5/1984 | Perry | 604/179 |
| 4,470,410 A | 9/1984 | Elliott | |
| 4,480,639 A | 11/1984 | Peterson et al. | |
| 4,569,348 A | 2/1986 | Hasslinger | |
| 4,591,356 A * | 5/1986 | Christie | 604/179 |
| 4,799,923 A * | 1/1989 | Campbell | 604/179 |
| 4,870,976 A * | 10/1989 | Denny | 128/877 |
| 4,917,112 A | 4/1990 | Kalt | |
| 4,919,654 A * | 4/1990 | Kalt | 604/180 |
| 4,966,590 A * | 10/1990 | Kalt | 604/180 |
| 5,188,608 A * | 2/1993 | Fritts | 604/179 |
| 5,403,285 A * | 4/1995 | Roberts | 604/179 |
| 5,549,567 A * | 8/1996 | Wolman | 604/179 |
| 5,664,581 A | 9/1997 | Ashley | |
| 5,897,519 A * | 4/1999 | Shesol et al. | 602/79 |
| 5,918,599 A | 7/1999 | Shesol | |
| 6,258,066 B1 * | 7/2001 | Urich | 604/174 |

* cited by examiner

*Primary Examiner* — Kevin C Sirmons
*Assistant Examiner* — Andrew Gilbert

(57) ABSTRACT

An assembly structured to secure a catheter, such as an IV tube to a predetermined portion of a patient's body such that the IV tube is anchored adjacent an entry site. A base is structured and configured to engage the predetermined body portion and includes an opening for exposure of and access to the entry site. A support member is selectively positionable at variable locations relative to the opening in adjacent relation to the entry site such that the IV tube is mounted on an exterior or exposed portion of the support member so as to access the entry site through the opening and eliminate any type of adhesive strip or like connector contacting or being secured to the patient's skin.

31 Claims, 18 Drawing Sheets

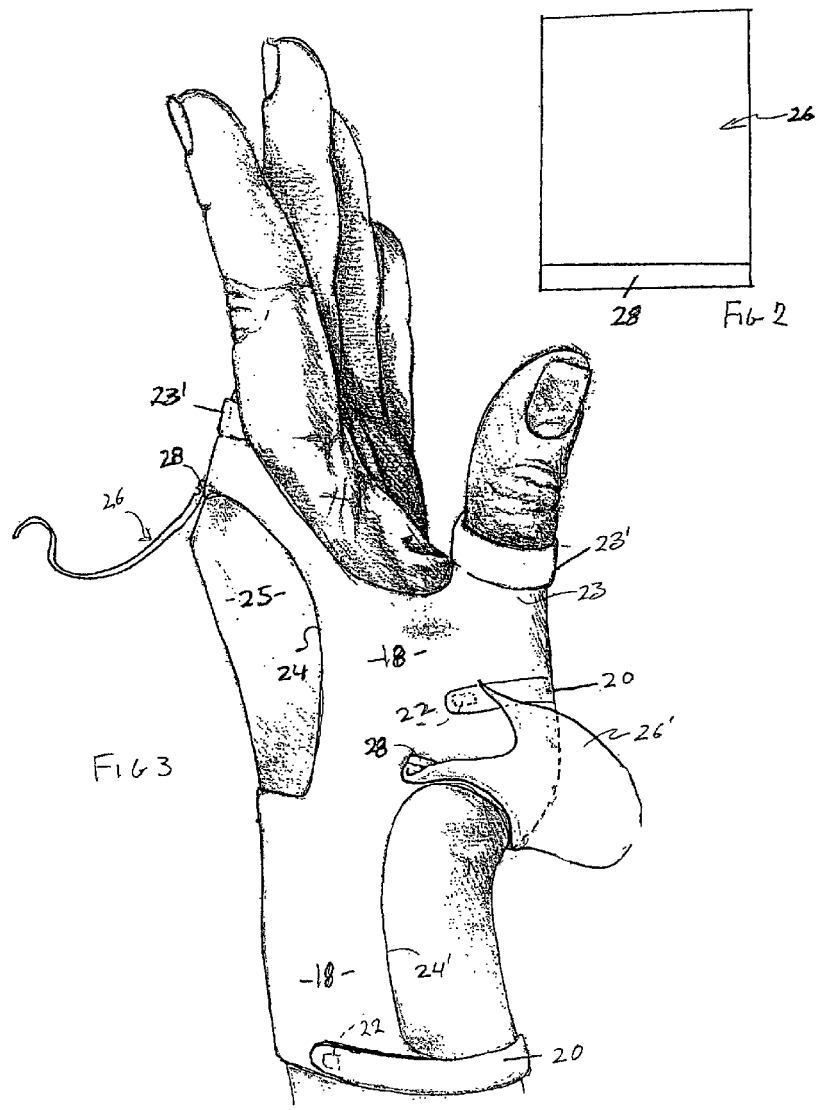

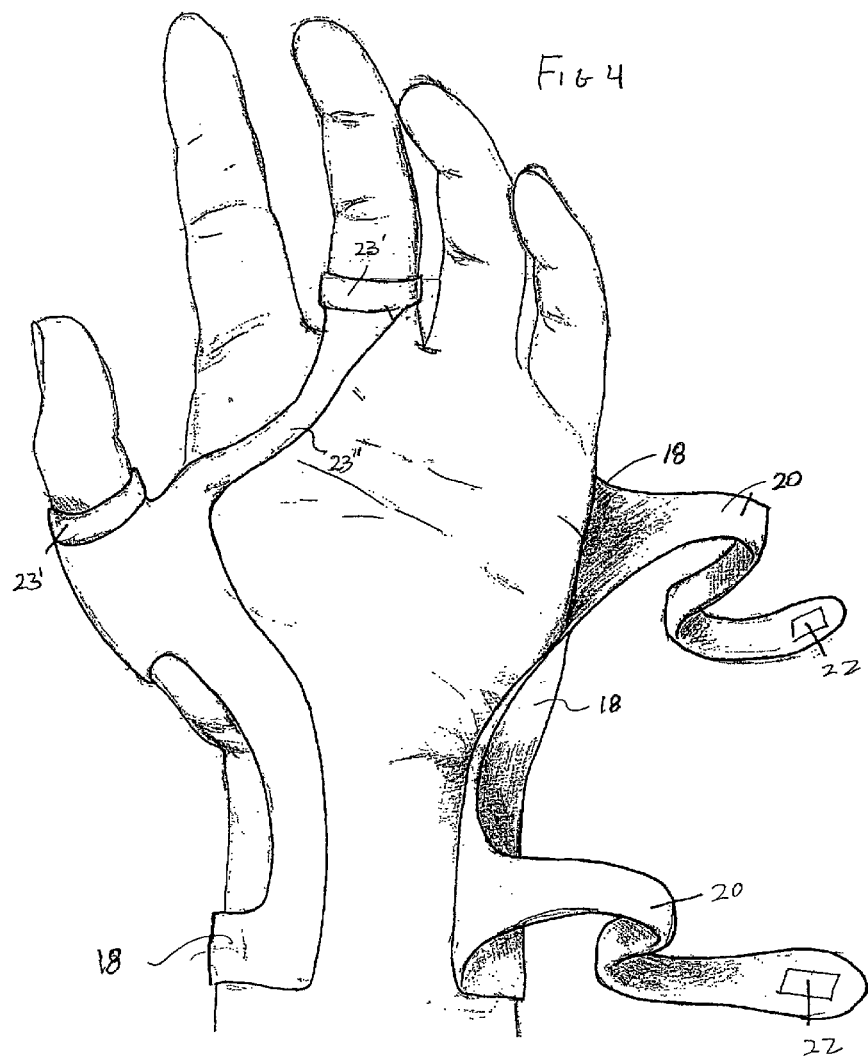

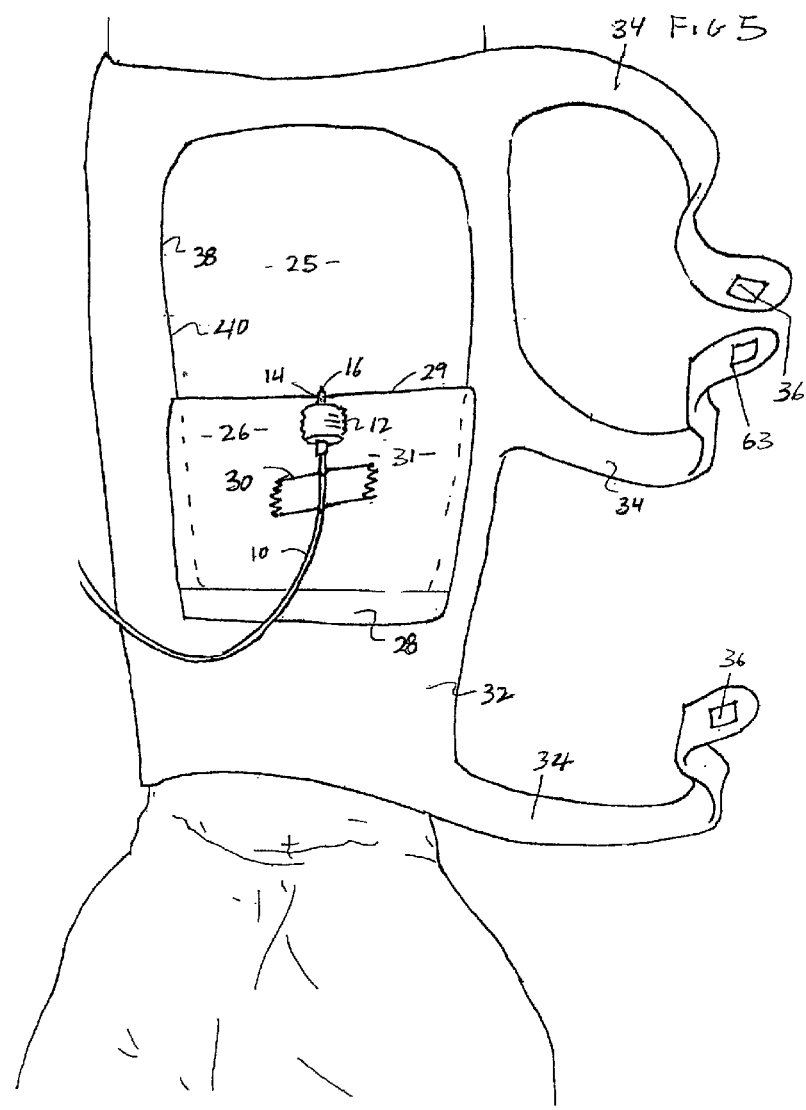

CATHETER SECUREMENT ASSEMBLY

BACKGROUND OF THE INVENTION

1. Field of the Invention

This invention is directed to an assembly for securing a catheter structure, such as an IV tube or the like, at an entry site of a patient's body such that the anchoring thereof is stable and accomplished without contacting the patient's skin with any type of adhesive strip or other attachment structure.

2. Description of the Related Art

Medical treatment of a patient, particularly one who is hospitalized, frequently involves the attachment of a catheter or like tubular structure to various portions of the patient's body. Most commonly an intravenous tube (IV) includes a hub and a penetrating needle, which enters a blood vessel for providing the patient with blood, plasma, medicine or other fluids. It is also common practice to maintain the catheter in attached relation to the patient for extended periods. In doing so it is important that the IV tube or other catheter is adequately secured in its intended location in a manner which reduces the possibility of inadvertent removal due to movement of the patient and/or the source of fluid being administered.

Conventionally the anchoring or attachment of various types of catheters to the patient's body involve the use of adhesive tape or strips typically wrapped around a hub or other adjacent portion of the catheter structure. The adhesive coating or backing of the tape or strip is then secured directly to the skin of the patient adjacent to the entry site of the catheter. It is also common practice to use a plurality of such adhesive tape strips, wherein at least one strip is disposed immediately adjacent to the entry site and one or more additional strips are disposed in spaced relation thereto. In the latter application of a plurality of adhesive connectors, there is typically concern for the inadvertent removal due at least partially to the involuntary or voluntary movement of the patient. While adhesive tape, strips and like connectors are used extensively in the medical field it has long being recognized that such means of catheter securement involves numerous problems and disadvantages.

More specifically, the adhesive material directly contacting the patient's skin, while possibly including some type of anti-bacterial agent, frequently causes skin irritation particularly when the catheter is secured to the entry site for prolonged periods. In addition, regardless of the precautions taken, irritation to patient's skin may occur particularly when the patients are sensitive to adhesive material and/or other chemical agents. Also, elderly patients who commonly have thin and/or friable skin may encounter damage or reactions not only because of the adhesive material but because the adhesive tapes or connectors may have to be frequently replaced. In the treatment of hospitalized patients it is not uncommon for the adhesive tape connectors to loose their binding force as the patient perspires or when the adhesive is inadvertently contacted by liquid spills at or adjacent to the entry site. Further, it is common practice to replace the IV tubing or other catheter devices on a regular basis thereby requiring periodic removal of the adhesive strips and replacement of new adhesive connectors, substantially in the same location.

In light of the above noted disadvantages and problems associated with securing a catheter at a predetermined location adjacent to a preferred entry site, there have been attempts in the medical equipment industry to develop various types of anchoring or securement structures, which better facilitate maintenance of the catheter on the patient's body. However, while generally acknowledging that contact of the adhesive material directly to the patient's skin is problematic, the majority of such catheter anchoring devices appear to be primarily concerned with the secure attachment of the catheter, IV tube, etc. in a manner which attempts to reduce or eliminate the possibility of the catheter becoming inadvertently dislodged, as set forth above.

In approaching such problems known devices initially appear to place the IV tube, tube hub, needle and other associated components in direct contact with the skin, whereby an outer wrap or strip of material is secured about the IV tube and catheter structure in overlying relation thereto. In spite of the sometime complex nature of such anchoring devices, adhesive tape or like connectors are still used to secure the hub portion directly adjacent to the entry site in a manner which allows the adhesive material to contact the patient's skin. Accordingly, while known devices of the type set forth above are assumed to be at least minimally operative for their intended function, they do not completely overcome the problems set forth above. By positioning adhesive material in contact with the patient's skin, skin irritations and/or infections caused by such direct and prolonged contact still exist. Also, the required practice of frequently replacing such adhesive connectors, when the intravenous tubing is removed and reattached, compounds the above noted problems.

Based on the above, there is a significant and long recognized need in the medical field for a novel catheter securement assembly which facilitates the attachment of one or more catheters to individual entry sites of a patient's body in a manner which eliminates direct contact between adhesive tape or like adhesive connector structures with the skin of the patient. In addition, such an improved and preferred securement assembly aids in the maintenance of healthy skin conditions of the patients by having all or at least a significant portion which is structured to allow the skin of the patient to be exposed to circulating air. Such exposure is accomplished even when certain predetermined portions of the patient are at least partially covered by the structural components of the improved catheter securement assembly.

Also, an improved catheter securement assembly should, in its various preferred embodiments, demonstrate sufficient versatility to be attached to different portions of the users body to which a catheter, IV tube, etc. is commonly secured. Such predetermined portions of the user's body includes hand or wrist, forearm, upper arm/elbow, ankle, head, neck and throat area and nose and face area. Moreover, while the various preferred embodiments of an improved catheter securement assembly may be primarily intended for use on human patients, the versatility thereof should be readily adapted, with little or no structural modification for use on other animals including, but not limited to, dogs, cats, etc.

SUMMARY OF THE INVENTION

The present invention is directed to an assembly structured to secure a catheter to an entry site on the patient's body. It is emphasized the term catheter may include a variety of different medical devices such as, but not limited to, an intravenous tube (IV). The catheter securement assembly of the present invention is structured to eliminate any irritation, discomfort or infection of a patient's skin immediately adjacent to the entry site or in a surrounding area of the predetermined portion of the patient's body at which the entry site is located. Moreover, physical attachment of the catheter is accomplished by eliminating any direct contact between an adhesive coating associated with a tape, strip, or other adhesive connector, and the skin of the patient as is common in current medical practice. The skin condition of the patient at the entry site or in surrounding relation thereto is further enhanced by the structuring of the material of the catheter securement assembly of the present invention from an air permeable, or breathable material.

The terms "air permeable" and "breathable" are intended to be substantially equivalent descriptive terms as used herein in describing the various preferred embodiments of the present invention. More specifically, the various components of the securement assembly of the present invention are preferably formed from a material having sufficient porosity to facilitate air flow therethrough and adequate air circulation on or about the skin of those portions of the patient's body which engage and/or are covered by operative components of the catheter securement assembly of the present invention. It is recognized that numerous air permeable or breathable materials are commercially available, such as one or more of the paper-like or synthetic materials which are commercially available. It is further emphasized that the material from which the various components of the present invention are formed is not intended to be limited to any specific material. To the contrary, the various components of the catheter securement assembly of the present invention may comprise any one of a plurality of materials which preferably, but not necessarily, have sufficient porosity and flexibility to overcome the disadvantages and problems typically associated with conventional or known catheter anchoring devices or procedures.

More specifically, the catheter securement assembly of the present invention comprises a base preferably formed of air permeable, breathable material having sufficient porosity to facilitate air circulation on or about the affected skin areas of the patient's body. As described in detail hereinafter, the base may assume a plurality of different structural configurations each intended to be associated with at least one predetermined portion of the users' body. As is generally recognized, catheters, including IV tubes can be applied to various portions of the patient's body including, but not necessarily limited to, the hand and wrist, forearm and/or elbow, lower leg and ankle, head, neck and throat, nose and face, etc. Accordingly, the various preferred embodiments of the present invention include a base dimensioned and configured to include an overall structure which facilitates its attachment to at least one of the aforementioned predetermined portions of the users's body.

Further, the base includes at lease one opening which is disposed in direct communicating relation to an entry site of the IV tube or like catheter structure. The opening is disposed, dimensioned and configured such that its periphery effectively surrounds the entry site. As will also be explained, at least some of the preferred embodiments of the present invention, dependent on the structural configuration of the base, include a plurality of openings disposed in spaced relation to one another. The relative location of the openings accommodates access to a plurality of different entry sites which may be associated with predetermined portions of the patient's body. Therefore, when a plurality of openings are utilized, they generally are disposed to coincide with "conventional" entry sites associated with the portion of the patient's body to which the base is connected.

In conforming the various embodiments of the base to the one or more predetermined portions of the patient's body, the base includes an attachment assembly preferably including at least one but more practically a plurality of stabilizing members. As such, the attachment assembly and in particular the one or more stabilizing members overly and at least partially surrounding appropriate areas associated with a predetermined body portion. The base is thereby secured in overlying relation to the predetermined body portion in a manner which properly positions the one or more associated openings relative to one or more intended entry sites. Further, the stabilizing members are disposed in their intended, attached positions utilizing any one of a plurality of different connectors. Such connectors include, but are not limited to, adhesive tabs, hook and loop type fasteners, snaps or a variety of other applicable connector members. These connectors are structured to either fixedly or removably secure the one or more stabilizing members in at least partially surrounding, attached relation to the intended body portion.

It is recognized that the IV tube or like catheter structure may be required to be periodically removed and/or replaced during the treatment period of the patient. Therefore the structural features of each of the preferred embodiments of the present invention facilitate either their repeated or continued use or alternatively are intended to be disposable and intended for only a single use. In the latter situation the aforementioned connector structures associated with the attachment assembly may fixedly or somewhat "permanently" secure the base to the patient, wherein the base may be cut or otherwise detached from the patient's body for removal and/or replacement of the associated catheter structure. As will also be evident hereinafter the catheter securement assembly of the present invention has sufficient versatility to allow only a portion thereof to be removed while allowing other operative components, such as a support member supporting the catheter structure, to be repeatedly attached to the same base or a plurality of different bases, dependent on the hygienic condition of the patient, base, support member, etc.

As set forth above, each of the preferred embodiments of the catheter securement assembly of the present invention comprises at least one support member secured to an exterior portion of the base and selectively disposable in overlying relation to one opening formed on the base. When the base includes a plurality of openings to be associated with different potential entry sites, a plurality of support members, equal in number to the number of openings, are utilized. Therefore, each opening includes a different support member movably secured to an exterior of the base and selectively disposable in overlying, at least partially covering relation to the associated opening. Because of a specific location of an entry site within a given opening may vary, the associated support member is structured to be selectively positioned at a location laterally adjacent to the entry site so as to properly support and secure the catheter or IV hub, needle, etc. in direct accessible relation to the entry site. As such, the one or more support members are structured to be disposed in overlying relation to variable portions of the associated opening in order that a formed peripheral, portion or edge thereof is disposed immediately adjacent to the entry site.

One feature of the present invention comprises the one or more support members being positioned and/or oriented to have an exposed or exterior surface or other exposed portion disposed and structured to have the catheter mounted thereon. Physical attachment of the catheter to the exterior of the support member may be accomplished by adhesive tape or strips, other adhesive connectors or a variety of other commonly known connectors including, but not limited to hook and loop type fasteners, clamps, snaps, etc. Regardless of the type connector utilized, the base, support member and opening are all cooperatively structured to prevent direct contact between an adhesive material associated with any type of connector and the skin of the patient. Discomfort, injury, infection, irritation, etc. to the patient's skin is thereby eliminated.

Therefore the present invention overcomes the long recognized disadvantages and problems associated with the conventional attachment procedures utilizing adhesive tapes, strips, etc. wherein an IV or like catheter structure is maintained adjacent an intended entry site. Further, the various preferred embodiments of the catheter securement assembly of the present invention are applicable for securement of a catheter structure to numerous predetermined portions of the patient's body to which a catheter structure is conventionally secured. Also, with little or no structural modification, one or more embodiments of the present invention may be utilized with human or animal patients without departing from the intended spirit scope of the present invention.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 2 is a front view of a support member to which the catheter structure is directly attached and which is adaptable for use with the various preferred embodiments of the catheter securement assembly of the present invention.

FIG. 3 is a side perspective view of the embodiment of FIG. 1.

FIG. 4 is a bottom perspective view of the embodiments of FIGS. 1 and 3.

FIG. 5 is a perspective view of another preferred embodiment of the present invention structured to be secured about the forearm of a patient.

FIG. 15A is a support member associated with the preferred embodiment of FIG. 15.

FIG. 15B is an end view of the embodiment of FIG. 15A.

Like reference numerals refer to like parts throughout the several views of the drawings.

DETAILED DESCRIPTION OF THE PREFERRED EMBODIMENT

Figure 1:
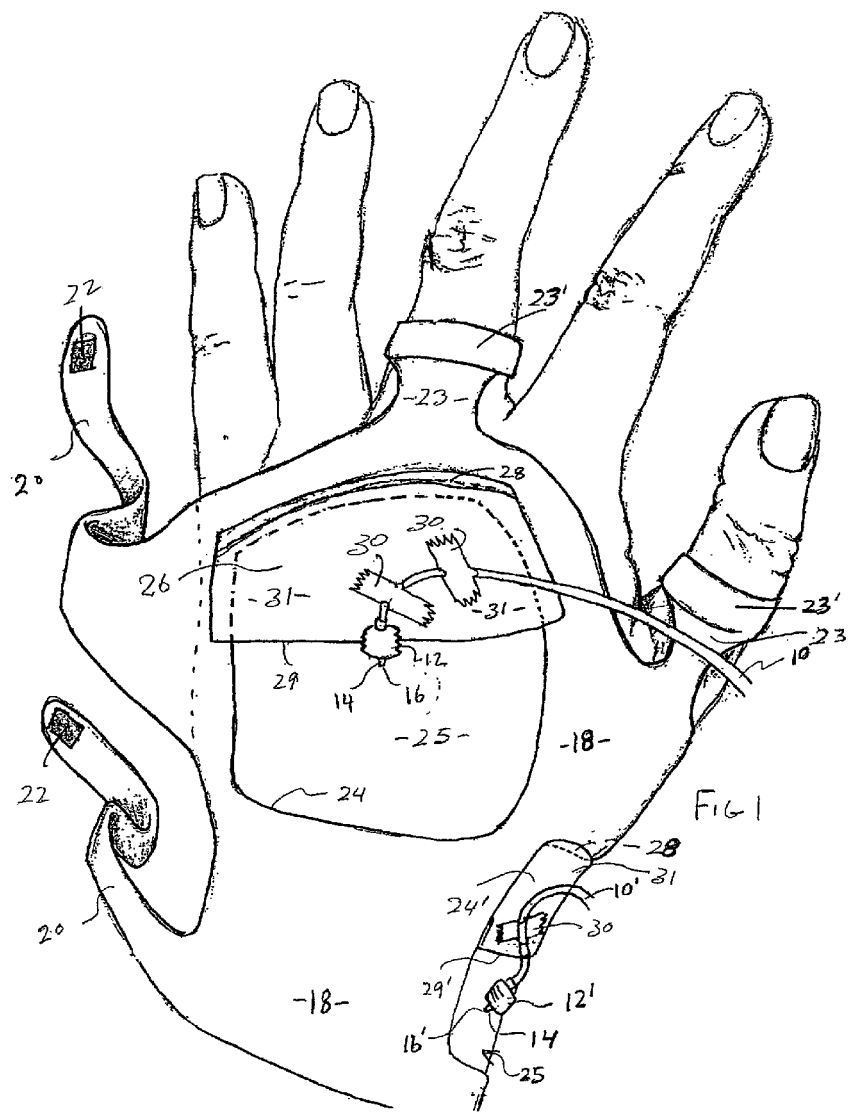
FIG. 1 is a perspective view of one preferred embodiment of the catheter securement assembly of the present invention structurally adapted to be mounted on or about a patient's hand.

As shown in the accompanying drawings, the present invention is directed to an assembly for the mounting and securement of a catheter structure 10 including, but not limited to, an IV tube as well as an accompanying hub 12 and penetrating needle or like instrument 14. As such, the various preferred embodiments of the catheter securement assembly of the present invention may comprise individual structural modifications which facilitate the mounting on or otherwise association with at least one predetermined portion of a patient's body.

As commonly recognized, catheters, including IV tubes, etc. may enter the patient's body at an entry site 16 wherein the specific location of the entry site 16 may vary. By way of example only, conventional entry sites may be located on the hand, lower arm or wrist, elbow, ankle, head, neck and throat, nose and face, etc. Accordingly, the various preferred embodiments of the catheter securement assembly of the present invention may be individually structured to be associated with one or more entry sites 16 located at one or more of such conventional entry site locations and still be encompassed within the intended spirit and scope of the present invention.

More specifically and with primary reference to FIGS. 1 through 4, the catheter securement assembly of the present invention includes a base 18 dimensioned, configured and generally structured to be secured to a hand portion of the patient. As such, the base 18 includes an attachment assembly including at least one but more practically a plurality of stabilizing members 20 which may have a somewhat elongated configuration of sufficient length to at least partially surround the hand (or other body portion) associated with a given entry site 16.

In order to secure the base 18 and catheter structure 10 in an operative position, each of the one or more stabilizing members 20 includes a connecting structure 22 preferably secured to an outer end thereof. The connecting structures 22 may comprise a variety of different connectors such as, but not limited to an adhesive tab, hook and loop type fastener, snap, clamp, etc. When disposed in a "closed" or attached position as best shown in FIG. 3, each of the one or more stabilizing members 20 has the connecting structure 22 removably or fixedly secured to a correspondingly located exterior surface of the base 18.

In that the embodiment of FIGS. 1 through 4 is structured to be mounted on or about a hand of a patient, the attachment assembly further comprises additional or supplementary stabilizing members 23. Each of the one or more stabilizing members 23 further includes an annulus or ring like structure 23' designed to fit about and/or otherwise removably engage individual fingers of the hand of the patient. As best shown in FIG. 4 the ring members 23' may also be interconnected to one another by a flexible material bridge 23" in order to provide further stability and enhanced securement of the base 18 to the hand or predetermined body portion of the patient.

The attachment assembly and in particular the one or more stabilizing members 22 and 23 serve to securely fasten the base 18 in an intended orientation relative to the predetermined portion of the patient's body, such as the hand as shown in FIGS. 1 through 4. However, the securement of the base 18 in the operative position shown in these Figures still allows at least some minimal adjusting movements in order to properly locate or orient the base 18 and one or more openings 24 and 24' relative to one or more entry sites 16 and 16'. Therefore, the base further includes one or more openings 24 and 24' formed therein and disposed and dimensioned to directly communicate with the skin area 25 directly associated with the intended entry site 16 or 16'. The one or more openings 24 and 24' may vary in size and shape dependent on the structure of the base and the predetermined portion of the patient's body on which the base is mounted.

Another feature included in the various preferred embodiments of the present invention comprises at least one support member 26. The support member 26, shown in detail in FIG. 2, includes a connecting structure 28 which may preferably be in the form of an adhesive strip securable to an exterior surface of the base 18 such as adjacent a periphery of an associated opening 24 and/or 24'. Further, the one or more support members 26 and 26' are formed of a material having sufficient flexibility and being otherwise structured to be selectively oriented in overlying and covering relation to at least a portion of the corresponding openings 24 and 24'. The flexibility of the support members 26 or 26' allows it to be folded, overlapped or otherwise oriented generally in a manner demonstrated in FIG. 1. The flexibility of the support member 26 or 26' thereby allows its selective positioning in overlying relation to variable portions of the opening 24 in order that at least one portion thereof as at 29 is disposed in laterally adjacent relation to the entry site 16. Such selected, variable positioning of the support member 26 and/or 26' facilitates the mounting and/or attachment of the catheter 10 and/or hub 12 on an exterior or exposed portion 31, where at it is attached by adhesive tape, strips, or a variety of other connectors indicated as 30.

Accordingly the dimension and configuration of the one or more support members 26, 26' may vary in order to cooperate with and at least partially correspond to the dimension and configuration of an associated opening 24 or 24'. This further enables selective orientation in overlying or at least partially covering relation to variable portions of the opening 24 or 24' in order that the edge or other portion 29 will be positioned laterally adjacent to the entry site 16 and thereby facilitate mounting of the catheter structure 10, 12 on an outer exposed portion 31 thereof. As a result and as will be evident from a detailed description of each of the preferred embodiments of the present invention, any contact of an adhesive coating or other material directly with the skin 25 of the patient will be eliminated. This is due to the fact that the one or more connectors 30 utilized to mount the catheter 10, 12 to the entry site 16 will be secured to the exposed or exterior portion of the support member 24 or 24'.

It is emphasized that in the various preferred embodiments of the present invention, one feature thereof comprises the advantage associated with the forming of one or all of the structural components of the various embodiments of the catheter securement assembly from an "air permeable" or "breathable" material. These terms as used therein, are meant to be substantially interchangeable and be descriptive of a material having sufficient porosity to facilitate the flow of air or the circulation thereof about and into contact with portions of the patient's skin which are covered by the various components of the catheter securement assembly, regardless of the specific preferred embodiment being applied. Therefore, it is noted the base, one or more support members, one or more stabilizing members as well as other associated structural components of the plurality of preferred embodiments of the catheter securement assembly, may be formed from the air permeable or breathable material having sufficient porosity to facilitate exposure of the affected skin areas of the patient to air. As such, discomfort and/or irritation of the skin of the patient affected by the catheter securement assembly of the present invention is eliminated or significantly reduced by such air exposure. It is emphasized however, that in at least one preferred embodiment of the catheter securement assembly of the present invention, material other than the air permeable, breathable or porous material may be utilized and still be included within the intended spirit and scope of the present invention.

In the preferred embodiment of FIG. 5, the catheter securement assembly comprises a base 32 dimensioned, configured and structured to be mounted on a lower arm and/or wrist portion of the patient. As such, the attachment assembly associated with base 32 includes a plurality of stabilizing members 34 each having a connector structure 36 preferably secured to an outer end thereof. The connector structure 36 may be in the form of an adhesive tab or other type of connector used to secure the stabilizing members 34 in at least partially surrounding relation to the predetermined portion of the patient's body.

Similar to the other preferred embodiments of the present invention, the base 32 includes at least one opening 38 dimensioned and configured to directly communicate with the skin area 25 associated with the entry site 16. Also, the support member 26 includes the attachment structure or adhesive type connector 28 secured to the exterior of the base 32. As shown in the various preferred embodiments of the present invention the connector strip 28 may be located along at least a portion of the periphery of the respective support members 26 but is disposed and structured to allow a substantially free movement of the support member 26 in overlying relation to variable portions of the opening 40 formed in the base 32.

Therefore, regardless of the precise location of the entry site 16, the edge or periphery 29 can be easily and accurately positioned in immediate, laterally adjacent relation to the entry site 16 in order to provide direct access of the penetrating instrument 14 to the entry site 16. At the same time, the catheter or needle hub 12 and a remaining portion of the catheter tube is secured, as by connector 30, to an exterior and/or exposed portion 31 of the one or more support members 26. It is again emphasized that the flexibility of the support member 26 allows its selective positioning over variable portions of the opening 40 in order that the edge or other portion 29 may be disposed in direct, preferably laterally adjacent relation to the entry site 16, as set forth above.

Figure 6:
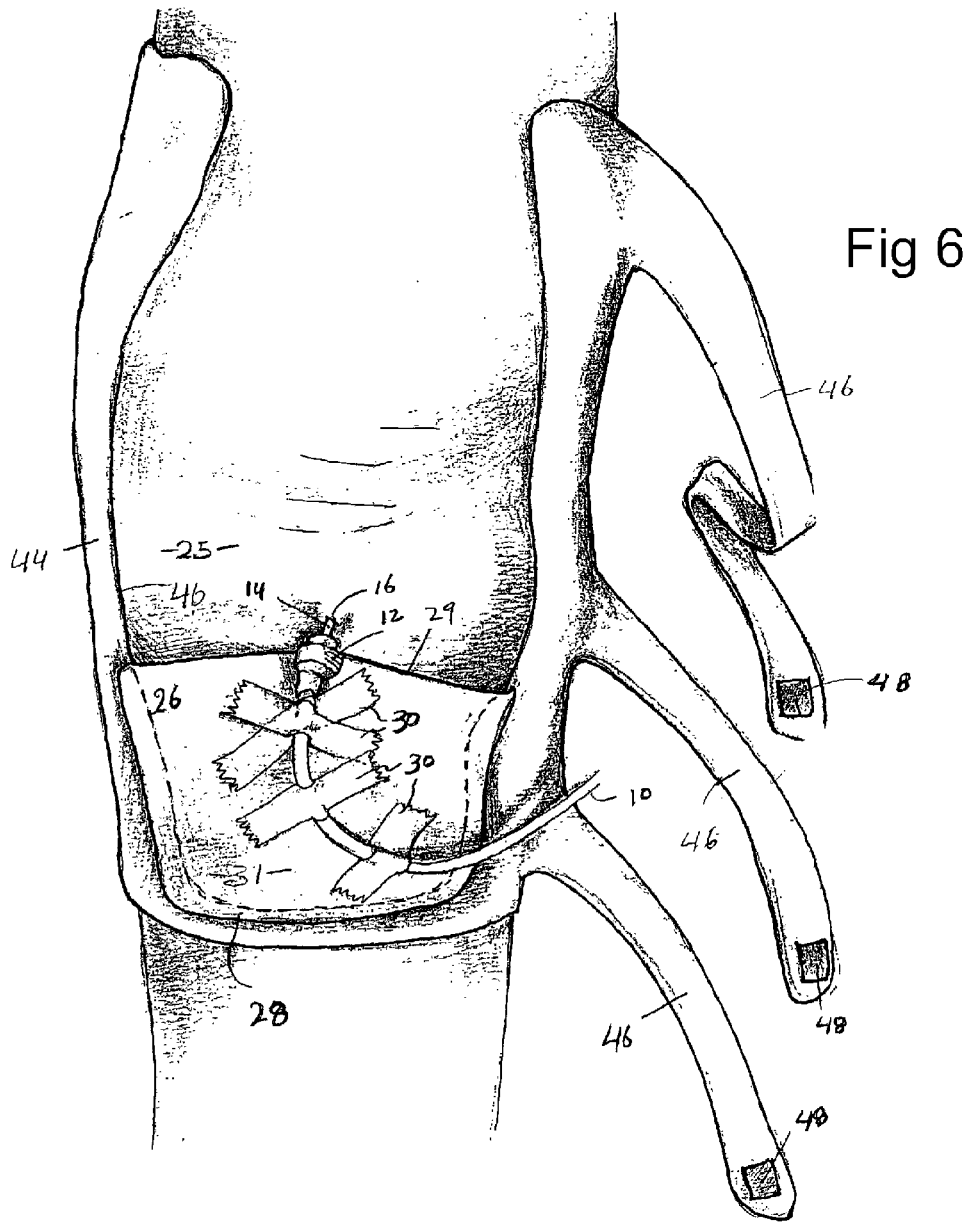
FIG. 6 is yet another preferred embodiment of the present invention structured to be secured about an elbow portion of the patient's body.
Figure 7:
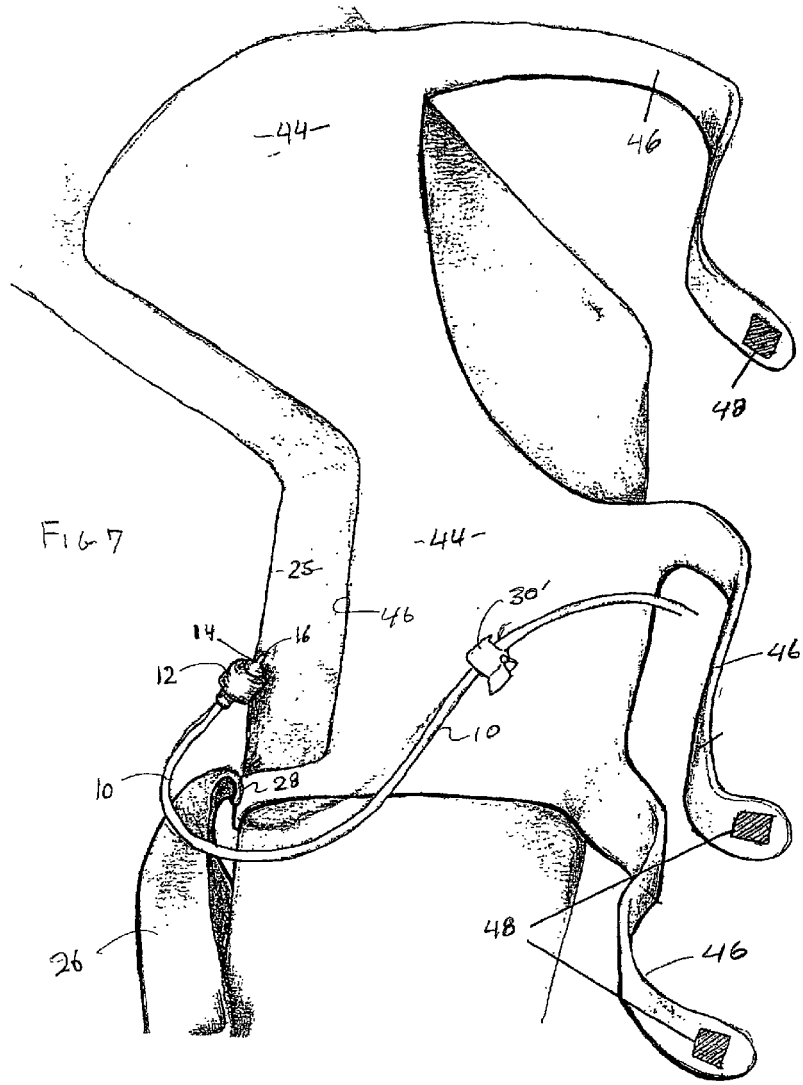
FIG. 7 is a side perspective view of the embodiment of FIG. 6.

Yet another preferred embodiment is shown in FIGS. 6 and 7 wherein the base 44 is structurally dimensioned and configured to be secured to and at least partially surround the elbow joint of a patient. As such, an attachment assembly associated with the base 44 includes a plurality of stabilizing members 46, each of which includes connectors 48 attached to the end thereof. Further, the base 44 includes at least one opening 40 disposed in direct communicating relation with the entry site 16. As with the other preferred embodiments of the present invention, the embodiment of FIG. 6 includes a support member 26 cooperatively dimensioned and configured to be secured to the exterior of the base 44, adjacent the corresponding opening 40 by means of the peripheral connector strip 28. The support member 26 is thereby selectively positionable over variable portions of the opening 40. As such, the catheter structure 10 including the hub 12 is mounted on an exterior or exposed portion 31 of the support member 26 thereby serving to maintain the connectors 30 and any adhesive material associated therewith out of direct contact with the skin 25 of the patient. As set forth above, the peripheral edge or like portion 29 formed by the selective positioning and orientation of the support member 26 is disposed in laterally adjacent relation to the entry site 16 to further facilitate proper support and securement of the catheter structure 10, including the hub 12.

Figure 8:
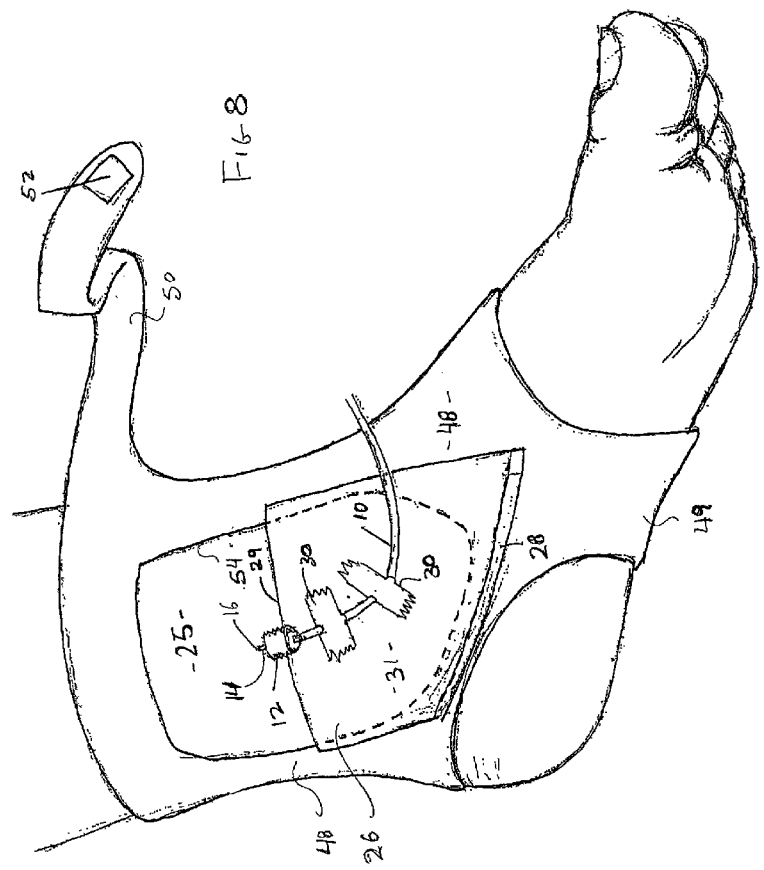
FIG. 8 is yet another preferred embodiment of the catheter securement assembly of the present invention structured to be secured about the lower leg, ankle and foot portion of the patient's body.
Figure 9:
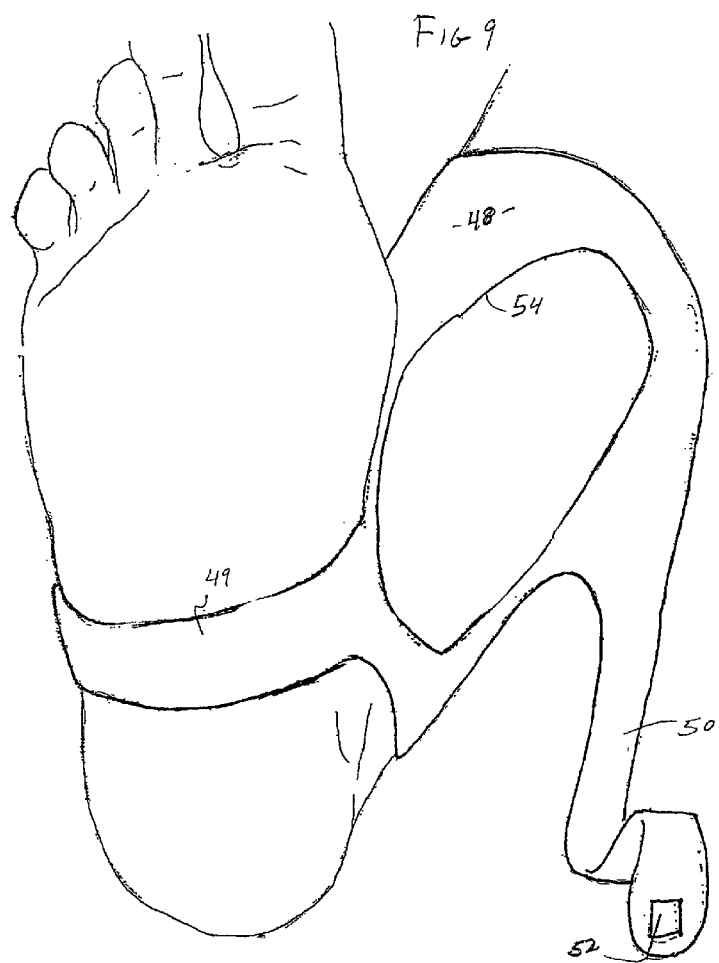
FIG. 9 is a bottom perspective view of the embodiment of FIG. 8.

With primary reference to FIGS. 8 and 9, yet another preferred embodiment of the catheter securement assembly of the present invention includes a base 48. The base 48 is specifically structured and configured to be mounted on and/ or at least partially surround a lower leg, ankle, and/or foot portion of the patient. In doing so, the base 48 includes a connecting bridge member 49 extending under the bottom or sole portion of the patient's foot. Therefore, the bridge member 49 can be considered a part of the attachment assembly.

The attachment assembly further comprises at least one stabilizing member 50 having a connecting structure 52 secured substantially at one end thereof. The connecting structure, as described in the embodiments of FIGS. 1 through 7, removably or fixedly engages the exterior surface of the base 48 when the stabilizing member 50 is wrapped around the lower portion of the leg, as disclosed. The base 48 also includes at least one opening 54 formed therein in communicating relation with the entry site 16. The embodiment of FIGS. 8 and 9 also includes a support member 26 mounted on an exterior of the base 48 due to the attachment of the adhesive or like connecting strip 28. Being so connected, the support member is disposable in overlying, at least partially covering relation to variable portions of the opening 54 dependent on the intended location of the entry site 16. The edge or like portion 29 is disposed in laterally adjacent relation to the entry site 16 thereby further facilitating proper placement and orientation of the catheter 10 including the hub 12 on the exterior or exposed portion 31 of the support member 26. Attachment of the catheter structure 10 to the exposed portion 31 of the support member 26 is accomplished by one or more connectors 30 which, as set forth above, may be in the form of adhesive tape, strips or other types of connectors. As such the connectors and any adhesive coating or backing associated therewith are maintained out of direct contact with the exposed skin 25 surrounding the entry site 16.

Figure 10:
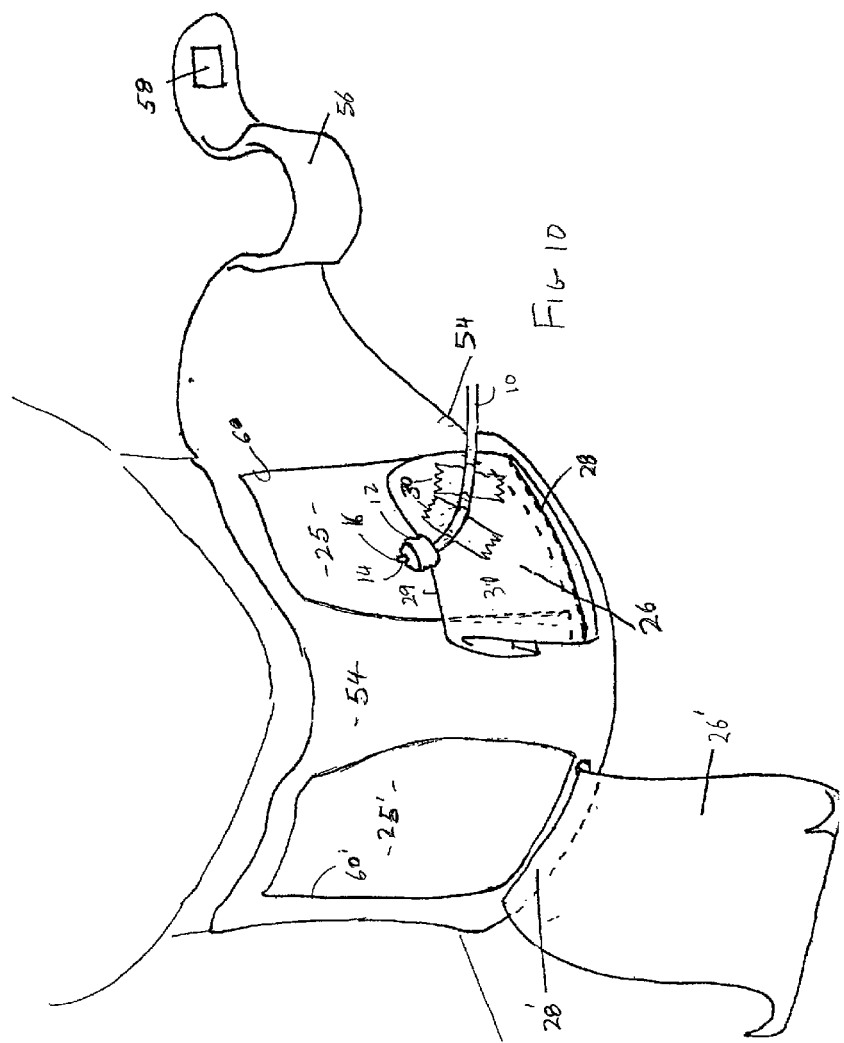
FIG. 10 is a front perspective view in partial cutaway of yet another preferred embodiment of the catheter securement assembly of the present invention structured to surround the throat and neck portion of a patient's body.
Figure 11:
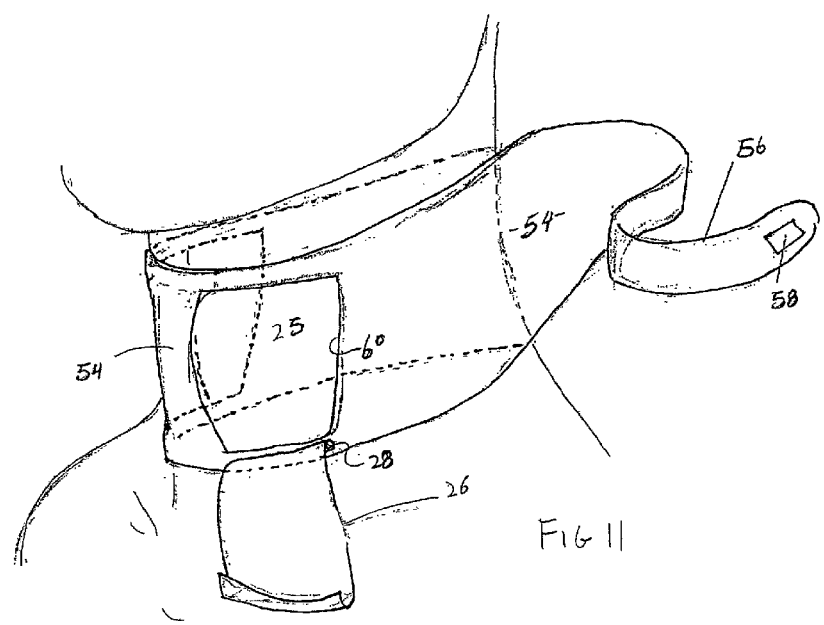
FIG. 11 is a side perspective view in partial cutaway of the embodiment of FIG. 10.

With primary reference to FIGS. 10 and 11, the catheter securement assembly of the present invention includes yet another preferred embodiment comprising base 54 having a somewhat elongated configuration terminating in at least one elongated stabilizing member 56. As with the previously described preferred embodiments, the stabilizing member 56 includes an adhesive tab or like connecting member 58 secured to one end thereof to facilitate removable or fixed attachment of the stabilizing member to an exterior surface of the base 54. As should be apparent the dimension and configuration of the base 54 is such as to surround the throat and neck area of the patient in order to at least partially isolate one or more entry sites 16.

As is well known in the medical profession it is common to establish entry sites for catheter structures 10 on substantially opposite sides of the patient's throat as best shown in FIG. 10.

Therefore, the base 54 includes a plurality of openings 60 and 60' each disposed in direct communicating relation with different exposed skin areas on opposite sides of the throat, indicated as 25 and 25'. For purposes of clarity only a single entry site 16 is disclosed and is surrounded by the periphery of opening 60. Moreover, the preferred embodiment of FIGS. 10 and 11 further includes a plurality of support members 26 and 26' each attached to an exterior of the surface 54 by means of connecting strips 28 and 28' which, as set forth above, may serve to movably connect the respective support members 26 and 26' adjacent to openings 25 and 25' respectively.

As with the previously described preferred embodiments, each of the support members 26 and 26' are positionable in overlying, substantially covering relation to variable portions of the respective openings 60 and 60' in order to mount a catheter structure 10 including hub 12 and penetrating member 14 in direct access to the entry site 16. As is also shown in FIG. 10, the support members 26 and 26' have sufficient flexibility to be oriented in an overlapped, folded or other preferred orientation so as to position the communicating edge or other portion 29 in immediate, laterally adjacent relation to the entry site 16. This further serves to facilitate a securement and mounting of the catheter structure 10, including hub 12 on the exposed or outer portion 31 of the support member 26 by means of connectors 30, as set forth above. Accordingly, connectors 30 and any adhesive material associated therewith are prevented from coming into direct contact with the exposed skin portions 25 or 25'.

Figure 12:
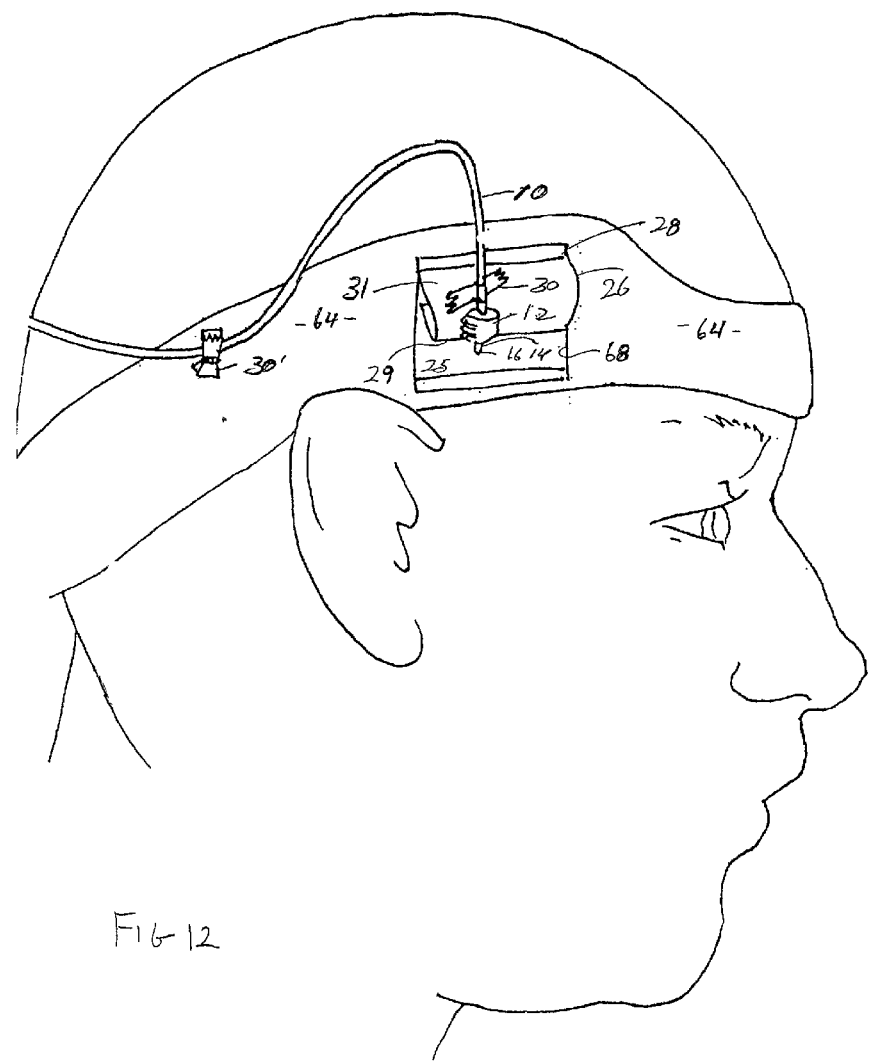
FIG. 12 is yet another preferred embodiment of the catheter securement assembly of the present invention structured to surround the head portion of a patient's body.
Figure 13:
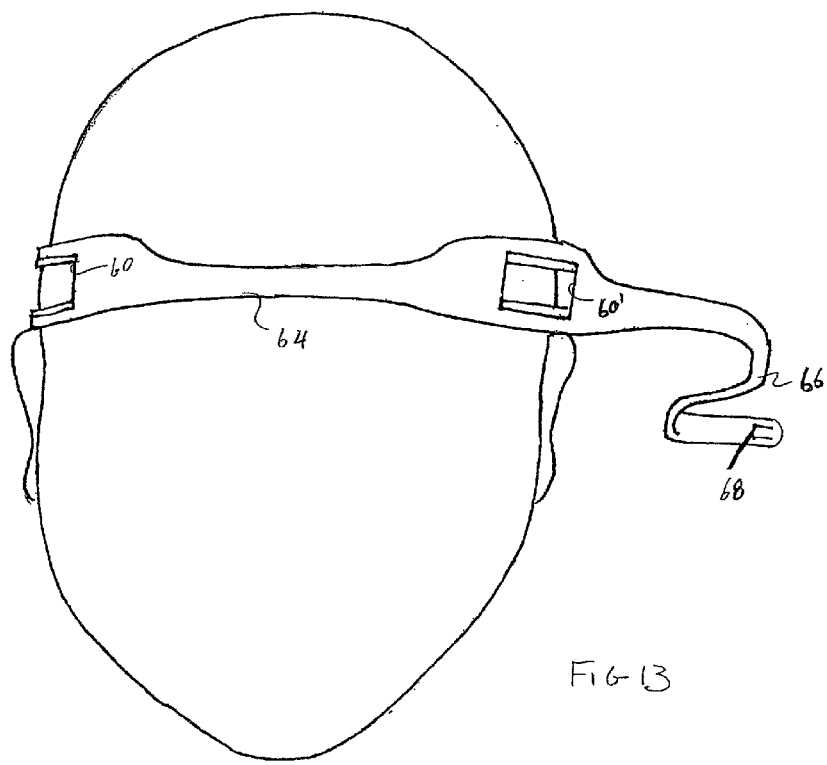
FIG. 13 is a front perspective view of the embodiment of FIG. 12.
Figure 14:
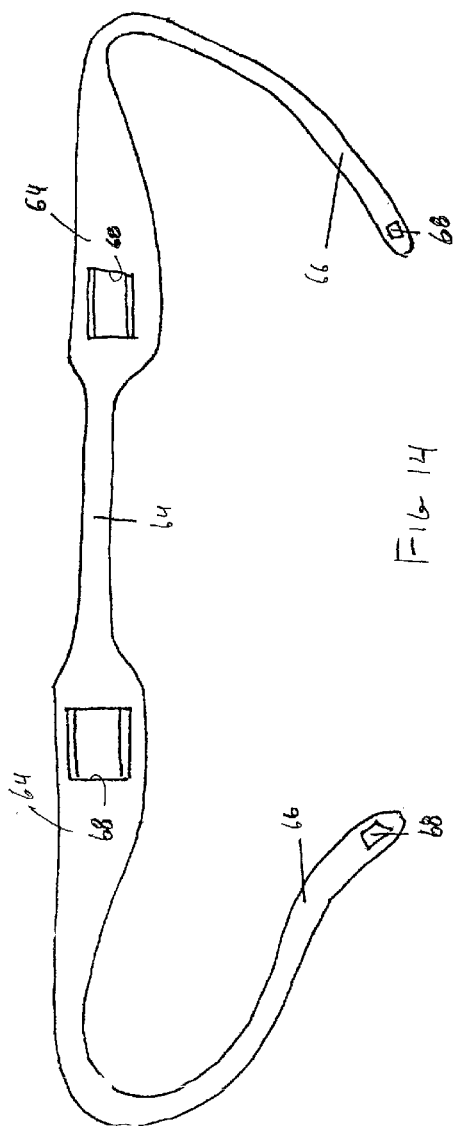
FIG. 14 is a front perspective view of the embodiment of FIGS. 12 and 13 being unattached to a patient's body.

An additional preferred embodiment of the catheter securement assembly is shown in FIGS. 12 through 14 and comprises a base 64 having an elongated configuration and including at least one but preferably two, spaced apart stabilizing members 66. Each of the stabilizing members include a connector structure 68 preferably in the form of an adhesive tab or other substantially equivalent structure. The longitudinal dimension of the base 64 is such as to completely surround a head of the patient substantially in overlying relation to the forehead and the oppositely disposed temple regions as best shown in FIGS. 12 and 13. When disposed in an operative position, the base 64 is dimensioned and configured to position two, spaced apart openings 68 and 68' at a location on the base 64 so as to overly predetermined skin areas 25 and associated portions of the patient's head. Each of the openings 68 and 68' is disposed in direct communicating relation with an actual or potential entry site 16 dependent on which side of the patient's head the catheter structure 10 is attached.

Further, each of the openings 68 and 68' is associated with a separate support member 26 secured to an exterior of the base by an attachment or connecting strip 28 and selectively positionable in overlying, at least partially covering relation to variable portions of the respective opening 68 or 68'. As such, the edge or other portion 29 is disposed in immediate, laterally adjacent relation to the actual entry site 16. The catheter structure 10 including the hub 12 is thereby secured to and mounted on an exposed and/or outer portion 31 of the support member 26 after it has been oriented in an overlapping, folded or other preferred orientation which best facilitates the disposition the portion 29 in the aforementioned immediate, laterally adjacent relation to the entry site 16. A connector 30 is used to secure the catheter structure 10 to the exposed portion 31 of the support member 26 and one or more additional connectors as at 30' may be used to further connect and stabilize the catheter tubing 10 to various portions of the exterior surface of the base 64 as also best shown in FIG. 12.

Figure 15:
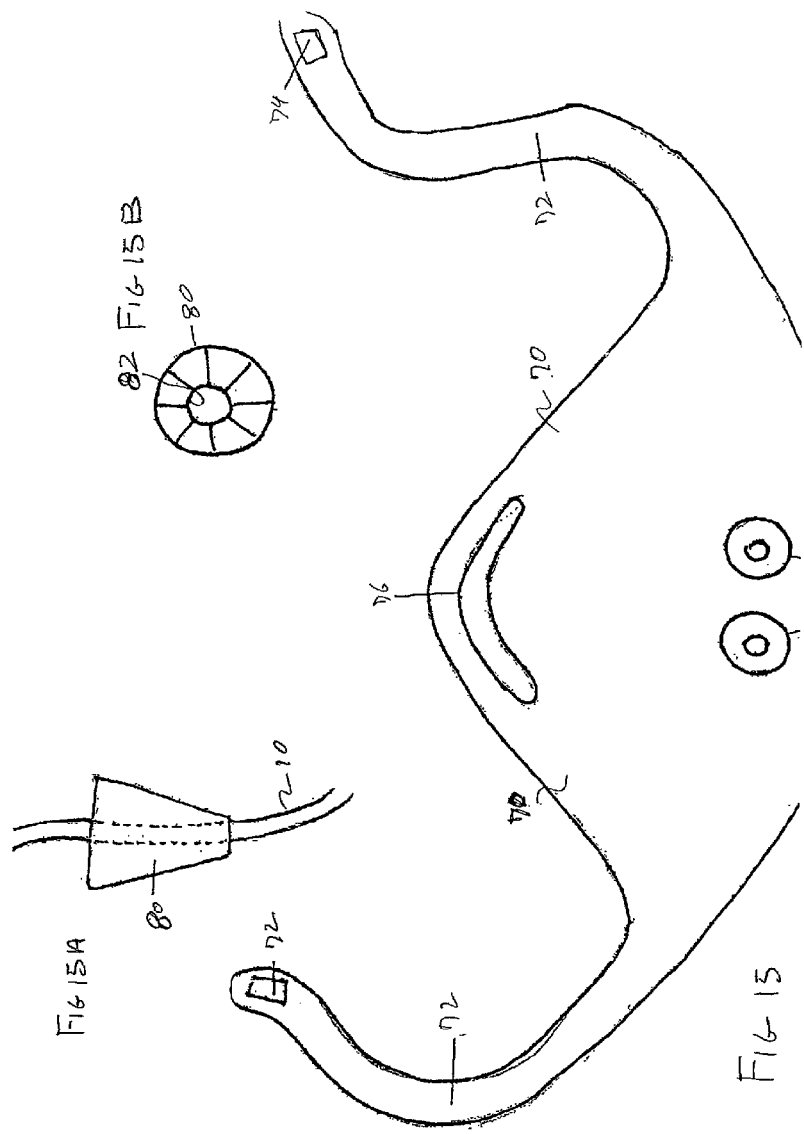
FIG. 15 is a front perspective view of yet another preferred embodiment of the catheter securement assembly of the present invention designed to be attached to the nose and/or face portion of patient's body.
Figure 16:
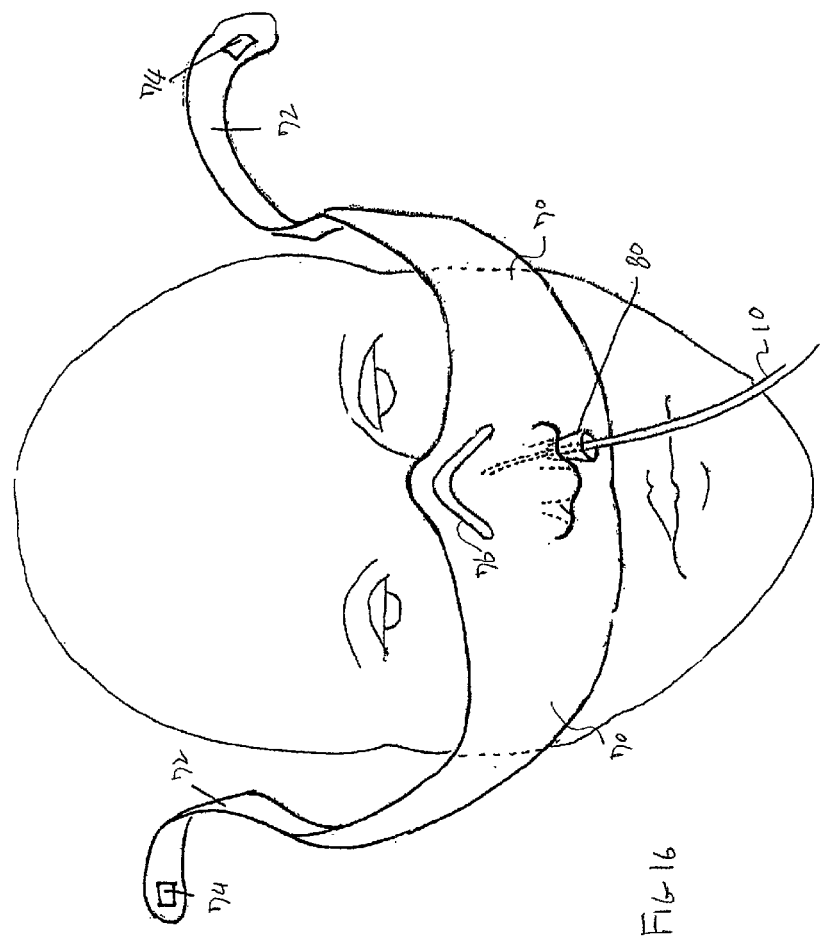
FIG. 16 is a front perspective view of the embodiment of FIG. 15 at least partially mounted about the nose and face portion of a patient's body.
Figure 17:
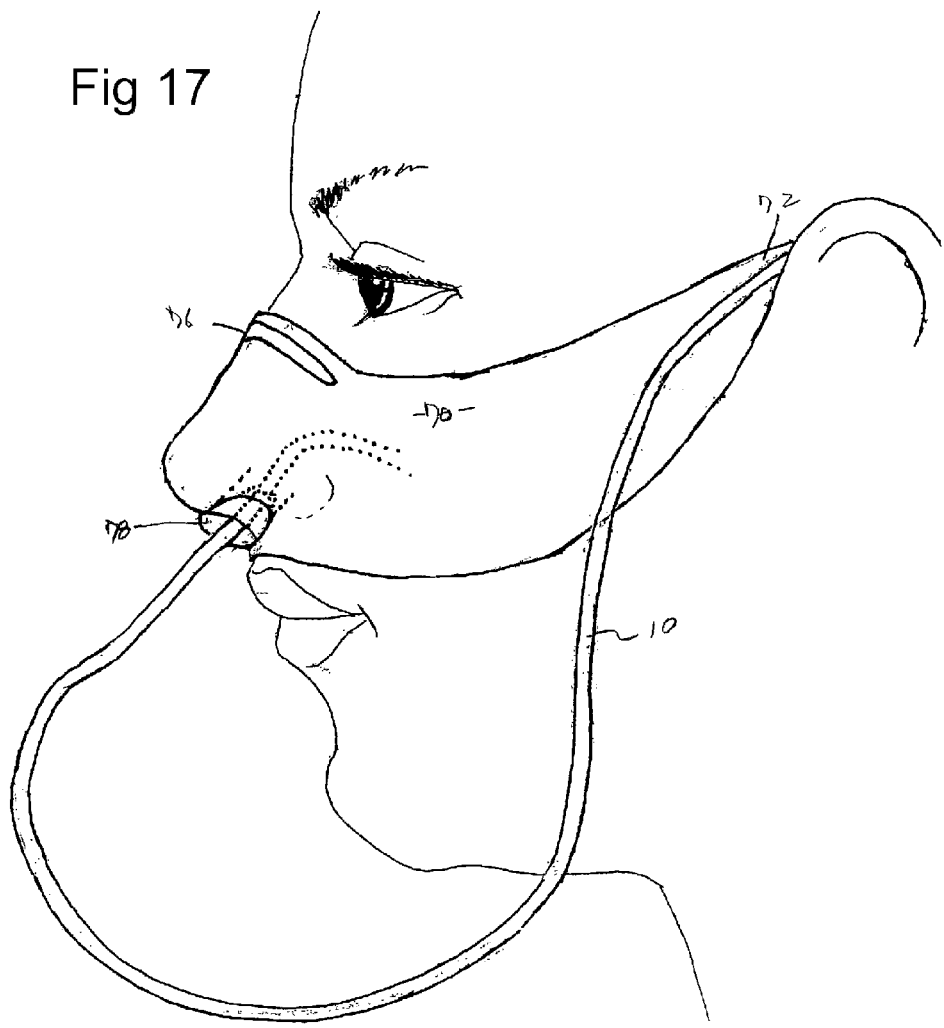
FIG. 17 is a side perspective view of the embodiment of FIGS. 15 and 16.

The catheter securement assembly of the present invention comprises yet another preferred embodiment disclosed in FIGS. 15 through 17. More specifically, a base 70 is dimensioned, configured, and structured to be secured in substantially overlying relation to the nose of the patient and about the face thereof as clearly demonstrated. The base 70 includes at least one but more practically two stabilizing members 72 disposed at and defining opposite ends of the base 70. Each of the stabilizing members 72 includes a connector structure in the form of an adhesive tab or like member 74. The connector structures 74 are designed to secure the base 70 in overlying relation to the face and the nose when attached to one another or to oppositely disposed ones of the stabilizing members 72. Further, an attachment assembly of the base 70 being at least partially defined by the stabilizing members 72 may also include a metallic or other malleable material member 76 designed to further secure and stabilize the base 70 about the exterior or bridge portion of the nose.

The base 70 further includes at least one but preferably a plurality of openings 78 each disposable in aligned relation with corresponding nostrils 79 of the nose of the patient. As should be apparent the embodiment of FIGS. 15 through 17 are designed to secure a catheter structure 10, such as an endotracheal tube, through the nasal passages of the patient by entering through one of the nostrils 79 of the patient's nose. In addition, the preferred embodiment of FIGS. 15 through 17 includes at least one support member 80 having a' tapered or somewhat conical configuration as best shown in FIGS. 15A and 15B. The support member 80 is secured to the catheter tube 10 by means of a centrally disposed channel or aperture 82 through which the catheter tube 10 passes. Due to the tapered or conical configuration of the support member 80, it is disposed within a selective one of the openings 78 and passes therethrough into the interior of a nostril 79 of the patient. Frictional engagement or a "wedging action" provides secure mounting of the catheter tube 10 and the support member 80 through a corresponding one of the openings 78. The support member 80 is thereby disposed to substantially cover variable portions of the respective openings 78 through which it passes. The mounting and securement of the catheter tube 10 to the exterior of the base 70 in the manner set forth above eliminates the use of any type of adhesive attachment or connector such as, adhesive tape, adhesive strips, etc. and further eliminates the possibility of such adhesive material coming into direct contact with exposed portions of the patient's skin.

Figure 18:
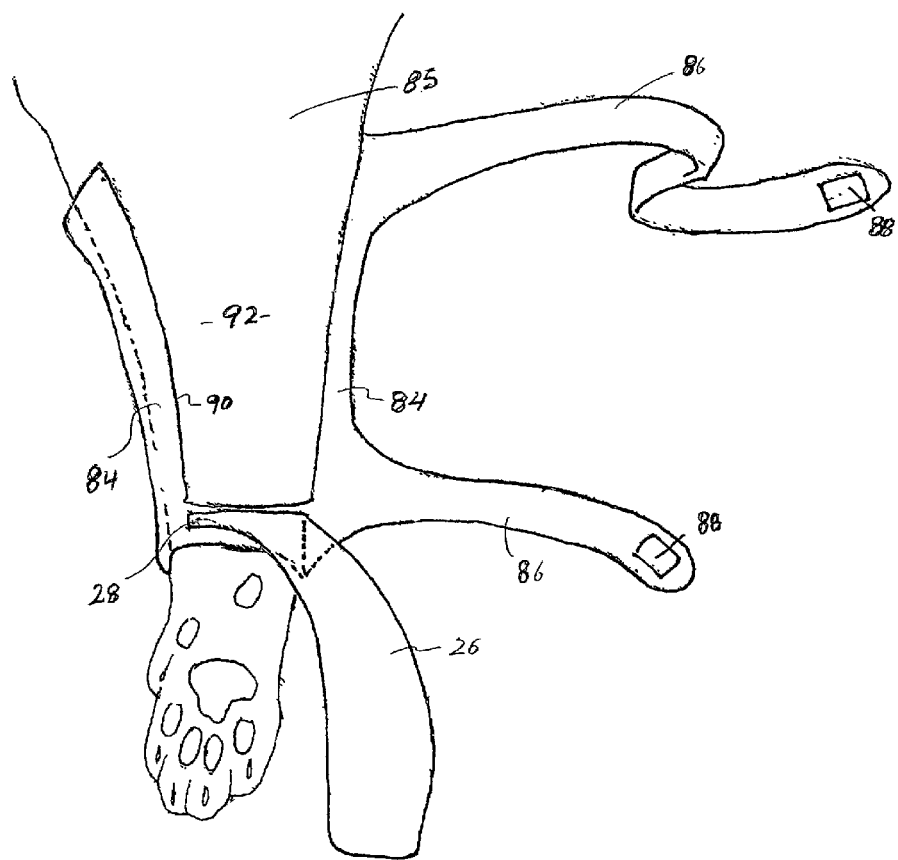
FIG. 18 is yet another preferred embodiment of the catheter securement assembly of the present invention structured to be mounted on an animal patient.
Figure 19:
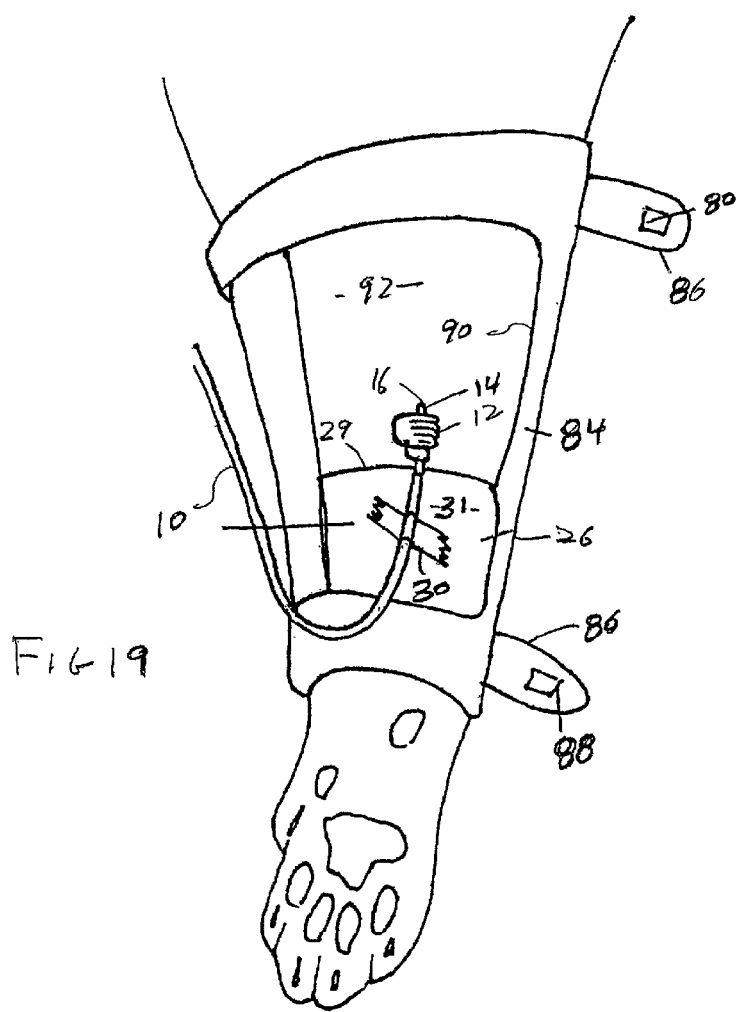
FIG. 19 is a perspective view of the embodiment of FIG. 18 shown in a closed operative position.

As set forth above, the catheter securement assembly of the present invention, while being primarily structured for use on a human patient, is equally applicable for use on other animals. Accordingly, as shown in the additional preferred embodiment of FIGS. 18 and 19, the catheter securement assembly of the present invention comprises a base 84 being configured to fit about a limb 86 of an animal such as dog, cat, etc. It is emphasized that the catheter securement assembly of the present invention is not limited to dogs, cats, etc. but can be used on a variety of different animals with little or no substantive structural modification. However, in each specific application, the base, such as at 84 will be dimensioned, configured and structured corresponding to the size and shape of the animal being treated.

Further, the base 84 includes an attachment assembly comprising at least one but preferably a plurality of stabilizing members 86 each having an elongated configuration so as to be disposed in surrounding relation to the limb 85 or other portion of the animal to which the catheter structure 10 is applied. Each of the stabilizing members 86 includes connector structures 88 preferably, but not necessarily, in the form of an adhesive tab, disposed to overly and be removably and/or permanently secured to the exterior surface of the base 84 as demonstrated in FIG. 19. The base 84 also includes at least one opening 90 disposed in surrounding directly communicating relation with a portion of the animal patient's skin 92 which surrounds or is generally associated with an actual or intended entry site 16. It is of course known that it is common medical practice to shave the treated skin area 92 so as to remove any type of fur or elongated hair that would interfere with the proper, accurate placement of the needle 14, hub 12 and/or the remainder of the catheter structure 10 relative to the entry site 16.

This additional preferred embodiment of the catheter securement assembly of the present invention further comprises a support member 26 secured to an exterior portion of the base by means of the aforementioned adhesive strip or like connector structure 28. Being so connected, the support member 26 can be disposed in overlying relation to variable portions of the opening 90 dependent upon the actual or intended location of the entry site 16. As such, the portion 29 is disposed in laterally adjacent relation to the entry site 16 thereby serving to effectively mount and support the catheter structure 10 including the hub 12 in its intended operative position through the opening 90 into direct access to the entry site 16. In its operative position, the catheter 10 is mounted on the exposed or exterior portion 31 of the support member 26. As also set forth above, the support member 26 has sufficient flexibility to be oriented so as to accurately position the portion 29 in laterally adjacent relation to the entry site 16. One or more connectors 30 serve to secure the catheter tube 10 and/or hub 12 to the exposed or exterior portion of the support member 26 as shown. Accordingly, the exposed skin area 92 is protected from any direct contact with one or more connectors 30 and/or any adhesive material associated therewith.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly to secure a catheter in a mounted operative position at an entry site located in a surrounding skin area of a patient's body, said assembly comprising:
   a) a base having an inside surface and an outside surface to be positioned in the mounted position with said inside surface of said base in contact with patient's body, and said base having
      I) at least one through access opening for direct open communication with the entry site and the surrounding skin area, and
      ii) a peripheral edge about said opening,
   b) a support member having a support exterior surface and a support interior surface configured to be mounted to the base outside surface while not extending beyond the base outside surface and having
      I) a proximal portion to connect said base,
      ii) a distally extending portion with a distal terminal edge, and
      iii) said distal terminal edge having
         a central portion, and
         a first and a second portion extending laterally in opposite directions from one another and the central portion,
   c) at least one connector disposed and structured to secure the catheter to the support member exterior surface,
   d) said distally extending portion being dimensioned such that, when said support member is mounted to the outside surface and disposed into said operative position overlying at least a portion of the opening, the central portion of said terminal edge is immediately adjacent said entry site, said first and second portions each extend laterally in opposite directions from one another and from the central portion to said peripheral edge about said opening, and e) said connector and said support member being cooperatively dimensioned, disposed and structured relative to one another and to said opening to securely maintain the catheter in the mounted operative position on said exterior surface of said support member and in segregated relation to the patient's skin, and wherein the base inside surface is free from adhesive.

2. An assembly as recited in claim 1 wherein said base comprises a plurality of stabilizing members disposed in spaced relation to one another, each of said stabilizing members dimensioned and configured to at least partially surround the hand of the patient's body.

3. An assembly as recited in claim 2 wherein each of said plurality of stabilizing members include a fastener disposed thereon and structured to maintain said plurality of stabilizing members in a closed position.

4. An assembly as recited in claim 3 wherein each of said stabilizing members comprises a substantially elongated configuration, said fasteners located adjacent at least one end of corresponding ones of said plurality of stabilizing members.

5. An assembly as recited in claim 1 wherein said base is formed from an air permeable material.

6. An assembly as recited in claim 5 wherein said support member is formed from an air permeable material.

7. An assembly as recited in claim 1 wherein said support member is formed from an air permeable material.

8. An assembly as recited in claim 1 wherein said support member is movably mounted on said base and variably disposable relative to said opening.

9. An assembly as recited in claim 8 wherein said support member is formed of a material having sufficient flexibility to overly variable portions of said opening.

10. An assembly as recited in claim 9 wherein said support member is selectively foldable relative to itself so as to overly different portions of said opening.

11. An assembly as recited in claim 8 wherein said support member is removably connected to said base and dimensioned and configured to extend from at least a periphery of said opening inwardly into an interior thereof.

12. An assembly as recited in claim 8 wherein said support member is connected to said base outside surface and is selectively positionable in overlying relation to variable portions of said opening and into a laterally adjacent relation to the entry site.

13. An assembly as recited in claim 1 wherein said base comprises a plurality of openings formed therein in spaced relation to one another, each of said plurality of openings disposed in accessible relation to a different entry site.

14. An assembly as recited in claim 13 comprising a plurality of support members each movably connected to said base outside surface and disposable in overlying relation to at least a portion of a different one of said plurality of openings.

15. An assembly as recited in claim 14 wherein each of said support members is formed of a material of sufficient flexibility to be oriented in overlying relation to variable portions of a corresponding one of said openings and in laterally adjacent relation to a corresponding entry site.

16. An assembly as recited in claim 15 wherein said base is formed from an air permeable material.

17. An assembly as recited in claim 15 wherein each of said plurality of support members is formed from an air permeable material.

18. An assembly structured to secure at least one catheter adjacent to an entry site of a patient's body, said assembly comprising:

a) a base having a base exterior surface and a base inside surface mountable on a hand of a patient's body without adhesive contact on the body, b) at least one opening formed in said base and disposable in communicating relation to the entry site, c) a support member having a support exterior surface and a support inside surface and having a terminal edge movably mounted on said base exterior surface and selectively disposable into overlying relation with variable portions of said opening, and d) said support member having at least one connector structured to secure the catheter to said support exterior surface in communicating relation with the entry site through said opening with said edge in immediate and laterally extending relation to the entry site.

19. An assembly as recited in claim 18 further comprising an attachment assembly connected to said base and structured to mount said base on a hand of a patient's body associated with the entry site.

20. An assembly as recited in claim 19 wherein said attachment assembly comprises at least one stabilizing member connected to said base and structured to at least partially surround the hand of the patient's body.

21. An assembly as recited in claim 20 wherein said attachment assembly comprises a finger engaging structure disposed in removable attachment to a finger of the patient's body.

22. An assembly as recited in claim 18 wherein said base, said support member and said attachment assembly are all formed from an air permeable material.

23. An assembly as recited in claim 18 wherein said base comprises a plurality of openings formed therein in spaced relation to one another, each of said plurality of openings disposed in accessible relation to a different entry site.

24. An assembly as recited in claim 23 comprising a plurality of support members each movably connected to said base outside surface and disposable in overlying relation to at least a portion of a different one of said plurality of openings.

25. An assembly as recited in claim 24 wherein each of said support members are formed of a material of sufficient flexibility to be oriented in overlying relation to variable portions of a corresponding one of said plurality of openings and in laterally adjacent relation to a corresponding entry site.

26. An assembly structured to secure a catheter adjacent an entry site of a patient's body, said assembly comprising:

a) a base having an exterior surface and inside surface mounted in overlying relation to a hand of the patient's body while free of adhesive contact with the body, b) at least one opening formed in said base and disposed in communicating relation with the entry site so as to provide access to the entry site through said opening, c) at least one support member having a distal terminal edge and a support exterior surface and a support inside surface movably connected to said base exterior surface such that the terminal edge is selectively positionable in overlying relation to variable portions of said opening and in immediately laterally adjacent relation to the entry site, d) said support member and said opening cooperatively disposed and structured to securely orient the catheter in a predetermined operative position relative to the entry site, e) said predetermined operative position comprising the catheter secured to said support exterior surface by at least one connector and disposed through said opening into communication with the entry site, and f) said connector, said support member, and said opening cooperatively disposed and structured to securely orient a portion of the tubing adjacent said catheter exteriorly of said support member in segregated relation to the patient's skin.

27. An assembly structured to secure a catheter adjacent an entry of a patient's body, said assembly comprising:
    a) a base having an exterior surface and an inside surface mounted in overlying relation to a hand of the patient's body,
    b) two openings formed in said base and disposed thereon in accessible relation to a different entry site,
    c) two support members, each support member having a respective support inside surface movably mounted on said base exterior surface in at least partially overlying relation to a respective opening,
    d) each of said support members also having a respective exterior surface and a distal terminal edge and at least one connector disposed and structured to secure the catheter to said support exterior surface, with said terminal edge immediately adjacent the entry site and
    e) said support members, said connectors, and said openings cooperatively disposed and structured to maintain the catheter exteriorly of said base and support member and through said openings into communication with the entry site.

28. An assembly as recited in claim 27 wherein said attachment assembly comprises at least one stabilizing member connected to said base and structured to at least partially surround the patient's hand.

29. An assembly as recited in claim 27 wherein said base, said support member, and said attachment assembly are all formed from an air permeable material.

30. An assembly as recited in claim 27 wherein said base, said support member, and said attachment assembly are all formed from a material such that the assembly may be disposed of subsequent to each use.

31. An assembly structured to secure a catheter adjacent to an entry site of a patient's body, said assembly comprising:
    a) a flexible base having an outside surface and an opening having a closed perimeter;
    b) a stabilizing means for stabilizing the base with respect to a patient's body portion without adhesive;
    c) a flexible support having an exterior surface and an inside surface, the support inside surface releaseably secured to the outside surface of the base proximate the opening, and the support configured to cover variable portions of the opening to provide a support edge within the perimeter; and
    d) a connecting means for releaseably connecting a catheter to the support exterior surface;
    such that the base may be stabilized on a patient's body portion while a catheter is introduced to the patient's skin through the opening and secured to the support, thereby supporting the catheter with respect to the patient while, adjacent and distant from the entry site, the catheter is separated from the patient's skin and the skin is free from contact with adhesive.

* * * * *